(12) United States Patent
Woollam et al.

(10) Patent No.: US 7,283,234 B1
(45) Date of Patent: Oct. 16, 2007

(54) USE OF ELLIPSOMETRY AND SURFACE PLASMON RESONANCE IN MONITORING THIN FILM DEPOSITION OR REMOVAL FROM A SUBSTRATE SURFACE

(75) Inventors: John A. Woollam, Lincoln, NE (US); Blaine D. Johs, Lincoln, NE (US); Thomas E. Tiwald, Lincoln, NE (US); Martin M. Liphardt, Lincoln, NE (US); James D. Welch, Omaha, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 474 days.

(21) Appl. No.: 11/014,298

(22) Filed: Dec. 16, 2004

Related U.S. Application Data

(63) Continuation-in-part of application No. 10/238,241, filed on Sep. 10, 2002, now Pat. No. 6,937,341, and a continuation-in-part of application No. 09/756,515, filed on Jan. 9, 2001, now Pat. No. 6,455,853, and a continuation-in-part of application No. 09/162,217, filed on Sep. 29, 1998, now Pat. No. 6,034,777.

(60) Provisional application No. 60/609,339, filed on Sep. 14, 2004, provisional application No. 60/598,456, filed on Aug. 3, 2004, provisional application No. 60/530,416, filed on Dec. 17, 2003, provisional application No. 60/183,977, filed on Feb. 22, 2000.

(51) Int. Cl.
*G01J 4/00* (2006.01)
(52) U.S. Cl. ............... 356/369; 356/364; 356/365; 356/366; 356/367; 356/368

(58) Field of Classification Search ......... 356/364–369
See application file for complete search history.

(56) References Cited

U.S. PATENT DOCUMENTS 5,793,480 A * 8/1998 Lacey et al. .................. 356/73
5,900,633 A * 5/1999 Solomon et al. ............. 356/632

OTHER PUBLICATIONS

"Automatic Rotating Element Ellipsometers: Calibration, Operation and Real-Time Applications", Collins,Rev. Sci. Instrum., 61(8) (1990).
"Ceramic Surface Polariton Sensor"; Ribbing et al., Proc. SPIE, vol. 4103 (2000).

* cited by examiner

*Primary Examiner*—Gregory J. Toatley, Jr.
(74) *Attorney, Agent, or Firm*—James D. Welch

(57) ABSTRACT

Improved methodology for monitoring deposition or removal of material to or from a process and/or wittness substrate which demonstrates a negative e1 at some wavelength. The method involves detection of changes in P-polarized electromagnetism ellipsometric DELTA at SPR Resonance Angle-of-Incidence (AOI) to monitor deposition of and/or removal of minute amounts of materials onto, or from, said process and/or witness substrate. The methodology can optionally monitor ellipsometric PSI, and involves simultaneously or sequentially applying non-P-polarized electromagnetism at the same angle of incidence, or electromagnetic radiation of any polarization at a different angle-of-incidence and wavelength to the process or wittness substrate and application of conventional ellipsometric analysis.

19 Claims, 7 Drawing Sheets

USE OF ELLIPSOMETRY AND SURFACE PLASMON RESONANCE IN MONITORING THIN FILM DEPOSITION OR REMOVAL FROM A SUBSTRATE SURFACE

This application is a Continuation-In-Part of application Ser. No. 10/238,241 Filed Sep. 10, 2002 now U.S. Pat. No. 6,937,341, and of Ser. No. 09/756,515 Filed Jan. 9, 2001 now U.S. Pat. No. 6,455,853, and therevia Claims benefit of Provisional Application Ser. No. 60/183,977 Filed Feb. 22, 2000. This Application is further a Continuation-In-Part of application Ser. No. 09/162,217, now U.S. Pat. No. 6,034,777, Filed Sep. 29, 1998 via Pending application Ser. Nos. 10/829,620, Filed Apr. 22, 2004, and 10/925,333 Filed Aug. 24, 2004, and 09/419,794, Filed Oct. 18, 1999 (now U.S. Pat. No. 6,549,282), which was a CIP of said 777 Patent.

This Application directly Claims benefit from Provisional Applications 06/609,339, Filed Sep. 14, 2004; 60/598,456, Filed Aug. 3, 2004, and 60/530,416, Filed Dec. 17, 2003.

TECHNICAL FIELD

The disclosed invention relates to methodology for monitoring thin film deposition or removal from the surface of a substrate, and more particularly to methodology which combines Surface Plasmon Resonance (SPR) and Spectroscopic Ellipsometry (SE) techniques, involving use of process and/or wittness substrates with negative dielectric function e1, and small e2 in a specified wavelength range. Said method involves detection of changes in Ellipsometric Polarization State, (eg. DELTA or PSI), when P-polarized is caused to interact with a Sample at an Surface Plasmon inducing Resonant Angel-of-Incidence (AOI) to monitor deposition of and/or removal of minute amounts of materials onto, or from, a process and/or witness substrate, said monitoring being in combination with applying non-P Polarized electromagnetic radiation at the SPR resonance angle-of-incidence, and/or electromagnetic radiation of any polarization state at another angle-of-incidence, and conducting conventional ellipsometric analysis thereof simultaneously or sequentially.

BACKGROUND

Surface Plasmon Resonance (SPR) is a well-known optical diagnostics method used extensively by biologists to sensitively measure changes at surfaces. For insight it is noted that normally electromagnetic radiation reflects speculatly from smooth surfaces, or diffusely from rough surfaces, or reflects with combined specular and diffuse components. Surface Plasmon Resonance (SPR) refers to an unusual condition under which the light, rather than being immediately reflected, is absorbed and induces a surface "plasmon" or the like wave in the material. This occurs when using, for example, a gold film, and P-Polarized visible light (of say 650 nm wavelength) is caused to impinge upon thereupon at an SPR resonance angle of incidence of about 50 degrees to the normal to a surface thereof. This is described as a "resonant" condition for SPR. The P-Polarized light, (eg. which can comprise electromagnetic radiation of any functional wavelength), sets up a surface plasmon traveling wave along the surface of a metal. To date, SPR invariably uses either gold, silver, or other common metal for which plasmons are excited mainly by visible light. That is, the atomic nature of the material (metal) determines the resonant angle. In scientific terms, SPR can be performed on any material for which the real-part of the complex dielectric function (e1) is less than zero, in a wavelength region wherein imaginary part (e2) of the is complex dielectric function is not too great. Materials with negative real-part of dielectric function is useful wavelength ranges include especially low-mass materials, such as SiC, and Si-oxides. For example, SiC with real-part of dielectric constant. negative in spectral range 960 cm$^{-1}$ to 780 cm$^{-1}$, and AlN has range 610 cm$^{-1}$ to 800 cm$^{-1}$ negative dielectric function. SiO2 (quartz) is 1161 cm–1 to 1236 cm$^{-1}$. Hexagonal BN has useful ranges 1510 cm$^{-1}$ to 1595 cm–1 and 1367 cm$^{-1}$ to 1610 cm$^{-1}$, and cubic BN in range 1060 cm–1 to 1430 cm$^{-1}$. Graphite has possible resonance 867.8 cm–1 to 868.1 cm$^{-1}$; narrow but potentially useful. Heavily doped binary, ternary, and quaternary alloys of compound 3/I semiconductors move the resonance into the useful 2 to 18 micron spectral range (555 cm$^{-1}$ to 5000 cm$^{-1}$) for biological materials (see attached review article table and graphs). Other examples might be intercalation compounds of graphite, which dope as both donors and acceptors. Metals have negative real-part of dielectric function negative at long-wavelengths, but are difficult to excite, but are possibly useful for these measurements, especially ultra-smooth metals such as Ir.

Continuing, SPR can, sense both the time rate of change and the amount of attachment of biomaterial to a metal substrate. SPR is a known valuable method for development of new drug-release surfaces; development of sensors for toxins, bio-warfare threats, and diseases, development of new materials for implants in humans (such as stints and heart valves), and for numerous other biomedical and bioengineering applications. SPR is hundreds of times more sensitive than conventional spectroscopies for thin films. One example, (of hundreds), is in the monitoring of the attachment of toxins, (such as cholera), to surfaces functionallized by IgG protein. To date most applications have been in bio-material monitoring.

While the herein disclosed invention can be used in any material system investigation system such as Polarimeter, Reflectomerter, Spectrophotometer and the like Systems, an important application is with Ellipsometer Systems, whether monochromatic or spectroscopic. It should therefore be understood that Ellipsometry involves acquisition of sample system characterizing data at single or multiple Wavelengths, and at one or more Angle(s)-of-Incidence (AOI) of a Beam of Electromagnetic Radiation to a surface of the sample system. Ellipsometry is generally well described in a great many publication, one such publication being a review paper by Collins, titled "Automatic Rotating Element Ellipsometers: Calibration, Operation and Real-Time Applications", Rev. Sci. Instrum., 61(8) (1990).

A typical goal in ellipsometry is to obtain, for each wavelength in, and angle of incidence of said beam of electromagnetic radiation caused to interact with a sample system, sample system characterizing PSI and DELTA values, where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said sample system. This is expressed by:

$$TAN(\psi)\ e^{i(\Delta)}=r_s/r_p.$$

(Note the availability of the phase DELTA (Δ) data is a distinguishing factor between ellipsometry and reflectometry).

Ellipsometer Systems generally include a source of a beam of electromagnetic radiation, a Polarizer, which serves to impose a state of polarization on a beam of electromagnetic radiation, a Stage for supporting a sample system, and an Analyzer which serves to select a polarization state in a beam of electromagnetic radiation after it has interacted with a material system, and passed it to a Detector System for analysis therein. As well, one or more Compensator(s) can be present and serve to affect a phase angle between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). A preferred embodiment is a Rotating Compensator Ellipsometer System because, it is noted, Rotating Compensator Ellipsometer Systems do not demonstrate "Dead-Spots" where obtaining data is difficult. They can read PSI and DELTA of a Material System over a full Range of Degrees with the only limitation being that if PSI becomes essentially zero (0.0), DELTA can not then be determined as there is not sufficient PSI Polar Vector Length to form the angle between the PSI Vector and an "X" axis. In comparison, Rotating Analyzer and Rotating Plarizer Ellipsometers have "Dead Spots" at DELTA's near 0.0 or 180 Degrees and Modulation Element Ellipsometers also have "Dead Spots" at PSI near 45 Degrees). The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

Further, it is to be understood that causing a polarized beam of electromagnetic radiation to interact with a sample system generally causes change in the ratio of the intensities of orthogonal components thereof and/or the phase angle between said orthogonal components. The same is generally true for interaction between any system component and a polarized beam of electromagnetic radiation. In recognition of the need to isolate the effects of an investigated sample system from those caused by interaction between a beam of electromagnetic radiation and system components other than said sample system, (to enable accurate characterization of a sample system per se.), this Specification incorporates by reference the regression procedure of U.S. Pat. No. 5,872,630 to Johs et al. in that it describes simultaneous evaluation of sample characterizing parameters such as PSI and DELTA, as well system characterizing parameters, and this Specification also incorporates by reference the Vacuum Chamber Window Correction methodology of U.S. Pat. No. 6,034,777 to Johs et al. to account for phase shifts entered between orthogonal components of a beam of electromagnetic radiation, by disclosed invention system windows and/or beam entry elements. For insight, one embodiment of said method of accurately evaluating parameters in parameterized equations in a mathematical model of a system of spatially separated input and output windows, said parameterized equations enabling, when parameters therein are properly evaluated, independent calculation of retardation entered by each of said input window and said output window between orthogonal components of a beam of electromagnetic radiation caused to pass through said input and output windows, at least one of said input and output windows being birefringent, said method comprises, in a functional order, the steps of:

a. providing spatially separated input and output windows, at least one of said input and output windows demonstrating birefringence when a beam of electromagnetic radiation is caused to pass therethrough, there being a means for supporting a sample system positioned between said input and output windows;

b. positioning an ellipsometer system source of electromagnetic radiation and an ellipsometer system detector system such that in use a beam of electromagnetic radiation provided by said source of electromagnetic radiation is caused to pass through said input window, interact with said sample system in a plane of incidence thereto, and exit through said output window and enter said detector system;

c. providing a sample system to said means for supporting a sample system, the composition of said sample system being sufficiently well known so that retardance entered thereby to a polarized beam of electromagnetic radiation of a given wavelength, which is caused to interact with said sample system in a plane of incidence thereto, can be accurately modeled mathematically by a parameterized equation which, when parameters therein are properly evaluated, allows calculation of retardance entered thereby between orthogonal components of a beam of electromagnetic radiation caused to interact therewith in a plane of incidence thereto, given wavelength;

d. providing a mathematical model for said ellipsometer system and said input and output windows and said sample system, comprising separate parameterized equations for independently calculating retardance entered between orthogonal components of a beam of electromagnetic radiation caused to pass through each of said input and output windows and interact with said sample system in a plane of incidence thereto; such that where parameters in said mathematical model are properly evaluated, retardance entered between orthogonal components of a beam of electromagnetic which passes through each of said input and output windows and interacts with said sample system in a plane of incidence thereto can be independently calculated from said parameterized equations, given wavelength;

e. obtaining a spectroscopic set of ellipsometric data with said parameterizable sample system present on the means for supporting a sample system, utilizing a beam of electromagnetic radiation provided by said source of electromagnetic radiation, said beam of electromagnetic radiation being caused to pass through said input window, interact with said parameterizable sample system in a plane of incidence thereto, and exit through said output window and enter said detector system;

f. by utilizing said mathematical model provided in step d. and said spectroscopic set of ellipsometric data obtained in step e., simultaneously evaluating parameters in said mathematical model parameterized equations for independently calculating retardance entered between orthogonal components in a beam of electromagnetic radiation caused to pass through said input window, interact with said sample system in a plane of incidence thereto, and exit through said output window;

to the end that application of said parameterized equations for each of said input window, output window and sample system for which values of parameters therein have been determined in step f., enables independent calculation of retardance entered between orthogonal components of a beam of electromagnetic radiation by each of said input and output windows, and said sample system, at given wavelengths in said spectroscopic set of ellipsometric data, said calculated retardence values for each of said input window, output window and sample system being essentially uncorrelated.

No known references teach combined use of Surface Plasmon Resonance data which is obtained using P-Polarized electromagnetic radiation directed to a substrate surface at a Resonance angle-of-incidence, and conventional ellipsometric data which is obtained using other than P-Polarized electromagentic radiation applied at said SPR Resonance angle-of-incidence, or electromagneic radiation of any Polarization applied at other than said Resonance angle-of-incidence, in monitoring and optionally controlling thin film deposition or removal from the surface of said substrate.

DISCLOSURE OF THE INVENTION

The present invention recognizes that while Ellipsometry provides sensitivity to layers of material on the order of a nonometer, additional sensitivity to even thinner layers would be of benefit. The present invention provides for the use of the Surface Plasmon Resonance (SPR) effect in the monitoring of deposition or etching of thin layers of material, either independently or in symbiotic combination with practice of conventional ellipsometry. It is noted that the SPR technique requires that P-Polarized electromagnetic radiation be applied, whereas conventional ellipsometry can utilize any polarization orientation. The present invention then provides for application of P-Polarized and Non-P-Polarized electromagnetic radiation, simultaneously or sequentially, to a sample during deposition or removal of one or more thin films on a surface thereof.

A primary embodiment of the method of monitoring the deposition or removal of material from the surface of a substrate comprising the steps of:
 a) while material is being deposited or removed from said substrate surface, by causing electromagnetic radiation to impinge on, interact with and then enter a detector:
  obtaining ellipsometric data using P-Polarized electromagnetic radiation directed to a substrate surface at a Surface Plasmon Resonance Resonance angle-of-incidence to said sample surface, and
  simultaneously or sequentially obtaining conventional ellipsometric data using other than P-Polarized electromagentic radiation applied at said SPR Resonance angle-of-incidence, or electromagneic radiation of any Polarization applied at other than said SPR Resonance angle-of-incidence;
 b) analyzing said data to arrive at a thickness for deposited or removed material.

Said method can further comprise the step of controlling deposition or removal of material using said ellipsometric data.

Said method can involve said ellipsometric data obtained using P-Polarized electromagnetic radiation at the SPR resonance angle-of-incidence and data, and said ellipsometric data simultaneously or sequentially obtaining using other than P-Polarized electromagentic radiation applied at said SPR Resonance angle-of-incidence, or electromagneic radiation of any Polarization applied at other than said SPR Resonance angle-of-incidence, being analyzed simultaneously.

Another embodiment of the present invention is a method of monitoring deposition of, or etching of material from a sample surface comprising the steps of:
 a) providing an ellipsometer system comprising a source of electromagnetic radiation, a polarizer, a sample supporting stage, an analyzer and a detector and means for changing the angle-of-incidence at which the beam approaches said sample surface;
 a) placing a sample onto said sample supporting stage and by adjusting said polarizer, providing incident P-Polarized electromagnetic radiation to said sample surface, and while monitoring P-Polarized electromagnetic radiation reflected from said sample surface adjusting the angle-of-incidence until surface plasmon resonance occurs as evidenced by a large change in intensity or a determined ellipsometric PSI and/or DELTA, thereby indicating that the surface plasmon resonance angle-of-incidence has been identified;
 b) while depositing material onto or etching material from said sample surface, monitoring change in the ellipsometric PSI and/or DELTA which results from the P-Polarized electromagnetic radiation;
 c) said method further comprising providing incident non-P-Polarized electromagnetic radiation at the SPR Resonance, or another angle-of-incidence onto said sample surface such that it reflects into the same, or another detector, and determining a conventional ellipsometric PSI and/or DELTA therefrom;
 such that changes in said ellipsometric PSI's and/or DELTA's resulting from the P-Polarized and from the non-P-Polarized beams indicate deposition of, or etching of material from said sample surface.

It is noted that the P-Polarized and non-P-Polarized electromagnetic radiation can be simultaneously or sequentially applied to said sample surface, at the same, or at different angles-of-incidence. Also, where bio-materials are involved, the P-Polarized and non-P-Polarized electromagnetic radiation can comprise infrared wavelengths.

Still another embodiment of the presently disclosed invention is a method of controlling deposition or etching of thin layers of material to or from substrates comprising the steps of:
 a) providing a system for deposition of materials onto a process substrate placed therewithin, including a system for providing a beam of P-polarized electromagnetism and orienting it to direct said beam at an oblique angle of incidence to a surface of said process substrate, and/or a wittness substrate, reflect therefrom and enter a detector for monitoring ellipsometric PSI and DELTA of said process substrate and/or wittness substrate, said process substrate or wittness substrate having a negative e1 at at least one wavelength;
 b) adjusting the angle of incidence of the electromagnetic beam to a surface of said process substrate and/or wittness substrate until a decrease of intensity is noted at the detector for said at least one wavelength at which the e1 is negative, indicating formation of a surface plasmon in said process substrate and/or wittness substrate;
 c) while monitoring at least the ellipsometric DELTA of said process substrate and/or wittness substrate at said at least one wavelength at which its e1 is negative, causing process deposition of material onto said process substrate and/or wittness substrate; and
 d) utilizing change in said monitored DELTA to control the deposition procedure.

A modified embodiment of the disclosed invention is a method of controlling deposition or etching of thin layers of material to or from substrates comprising the steps of:
 a) providing a system for etching materials from a process substrate placed therewithin, including a system for providing a beam of P-polarized electromagnetism and orienting it to direct said beam at an oblique angle of incidence to a surface of said process substrate, and/or a wittness substrate, reflect therefrom and enter a detector for monitoring ellipsometric PSI and DELTA of said process substrate and/or wittness substrate, said process substrate or wittness substrate having a negative e1 at at least one wavelength;

b) adjusting the angle of incidence of the electromagnetic beam to a surface of said process substrate and/or wittness substrate until a decrease of intensity is noted at the detector for said at least one wavelength at which the e1 is negative, indicating formation of a surface plasmon in said process substrate and/or wittness substrate;

c) while monitoring at least the ellipsometric DELTA of said process substrate and/or wittness substrate at said at least one wavelength at which its e1 is negative, causing process etching of material from said process substrate and/or wittness substrate; and d) utilizing change in said monitored DELTA to control the etching procedure.

Said disclosed invention can involve both deposition and etching, and can be recited as a method of controlling deposition or etching of thin layers of material to or from substrates comprising the steps of:

a) providing a system for deposition and/or etching of materials onto or from a process substrate placed therewithin, including a system for providing a beam of P-polarized electromagnetism and orienting it to direct said beam at an oblique angle of incidence to a surface of said process substrate, and/or a wittness substrate, reflect therefrom and enter a detector for monitoring ellipsometric PSI and DELTA of said process substrate and/or wittness substrate, said process substrate or wittness substrate having a negative e1 at at least one wavelength;

b) adjusting the angle of incidence of the electromagnetic beam to a surface of said process substrate and/or wittness substrate until a decrease of intensity is noted at the detector for said at least one wavelength at which the e1 is negative, indicating formation of a surface plasmon in said process substrate and/or wittness substrate;

c) while monitoring at least the ellipsometric DELTA of said process substrate and/or wittness substrate at said at least one wavelength at which its e1 is negative, causing process deposition of and/or etching of material onto or from said process substrate and/or wittness substrate; and d) utilizing change in said monitored DELTA to control the deposition and/or etching procedure.

In any of the foregoing recitals, the wavelength at which the DELTA is monitored is preferably selected to be that at which said DELTA demonstrates the greatest sensitivity to change in the process substrate. For instance, where the material deposited or etched is biological, wavelengths in the infrared can be utilized.

In any of the foregoing recitals, the ellipsometric PSI of said process substrate and/or wittness substrate can also be monitored and change therein utilized in conjunction with said change in said monitored DELTA, to control the deposition and/or etching procedure in step d.

In any of the foregoing recitals, the beam of electromagnetic radiation can be spectroscopic and the ellipsometric PSI of said process substrate and/or wittness substrate is also monitored and change therein utilized in conjunction with said change in said monitored DELTA, to control the deposition and/or etching procedure in step d, and in Which the monitored PSI and DELTA are determined at a selection from the group consisting of:
the same wavelength; and
different wavelengths;

and preferably the wavelength chosen for monitoring at least one of said PSI and DELTA is that at which maximum sensitivty to process substrate change is demonstrated.

In any of the foregoing recitals, said wittness substrate can be monitored and be a selection from the group consisting of:
it is made from the same material as the process substrate;
it is made from the same material as the process substrate, but is of a different thickness;
it is made from a different material than the process substrate.

In any of the foregoing recitals, said process and wittness substrates can each be independently selected from the group consisting of:
gold;
silver;
iridium;
silicon;
gallium arsenide;
dielectrics such as TiO2;
gallium arsenide;
semiconductor with surface insulator layer(s);
doped semiconductor;
compensated semiconductor;
SiC;
AlN;
SiO2 (quartz);
hexagonal BN;
cubic BN;
Graphite;
Heavily doped binary, ternary, and quaternary alloys of compound 3/I semiconductors;

In any of the foregoing recitals, said said process and wittness substrates can be substantially identical, and monitored during processing of the process substrate but not the wittness substrate, and in Which data obtained from the monitoring of the wittness substrate is subtracted from data obtained from the monitoring of the process substrate in determining change in DELTA of the process substrate.

In any of the foregoing recitals,
the beam of electromagnetic radiation can be spectroscopic;
said said process and wittness substrates can be substantially identical and both are monitored during processing of the process substrate but into the wittness substrate;
data obtained from the monitoring of the wittness substrate can be subtracted from data obtained from the monitoring of the process substrate in determining change in DELTA of the process substrate; and
in which the ellipsometric DELTA is determined at more than one wavelength and utilized in control of the processing.

Further, in any of the foregoing recitals, is to be understood that the beam of P-polarized electromagnetism caused to approach the substrate can have intentionally associated therewith at least some non-P-polarized, (eg. S-polarized) electromagnetism, either simultaneously, or sequentially. An S component allows perfoming conventional ellipsometric evaluation of a substrate as said S component is not affected by the Surface Plasma Resonance (SPR) phenomona.

It is to be understood that the the procedure of obtaining ellipsometric data using P-Polarized electromagnetic radiation directed to a substrate surface at a Surface Plasmon Resonance Resonance angle-of-incidence to said sample surface, and simultaneously or sequentially obtaining conventional ellipsometric data using other than P-Polarized electromagentic radiation applied at said SPR Resonance angle-of-incidence, or electromagneic radiation of any Polarization applied at other than said SPR Resonance angle-of-incidence; followed by analyzing said data to arrive at a thickness for deposited or removed material can be applied to samples which are already fabricated.

Finally, while ellipsometric DELTA is generally more sensitive to layer thickness, and ellipsometric PSI is generally more sensitive to surface roughness and grading etc., it does occur that in some cases ellipsometric PSI provides better sensitivity to surface change than does ellipsometric DELTA. The foregoing recital focused on primary reference to ellipsometric DELTA, however, such is not always optimum. It is to be understood that in the foregoing, every instance of DELTA can be replaced with PSI and vice-versa and an alternative, and in some cases, superior, approach to monitoring surface change results. Claims which make this clear are presented herein.

SUMMARY OF THE INVENTION

It is therefore a purpose and/or objective of the disclosed invention to teach combined use of Surface Plasmon Resonance data which is obtained using P-Polarized electromagentic radiation directed to a substrate surface at a Resonance angle-of-incidence, and conventional ellipsometric data which is obtained using other than P-Polarized electromagnetic radiation applied at said SPR Resonance angle-of-incidence, or electromagneic radiation of any Polarization applied at other than said Resonance angle-of-incidence, in monitoring thin film deposition or removal from the surface of said substrate.

It is another purpose and/or objective of the disclosed invention to teach combined use of Surface Plasmon Resonance data which is obtained using P-Polarized electromagentic radiation directed to a substrate surface at a Resonance angle-of-incidence, and conventional ellipsometric data which is obtained using other than P-Polarized electromagentic radiation applied at said SPR Resonance angle-of-incidence, or electromagneic radiation of any Polarization applied at other than said Resonance angle-of-incidence, in controlling thin film deposition or removal from the surface of said substrate.

Other purposes and/or objectives of the disclosed invention will become apparent from a reading of the Specification and Claims.

DETAILED DESCRIPTION

Figure 1:
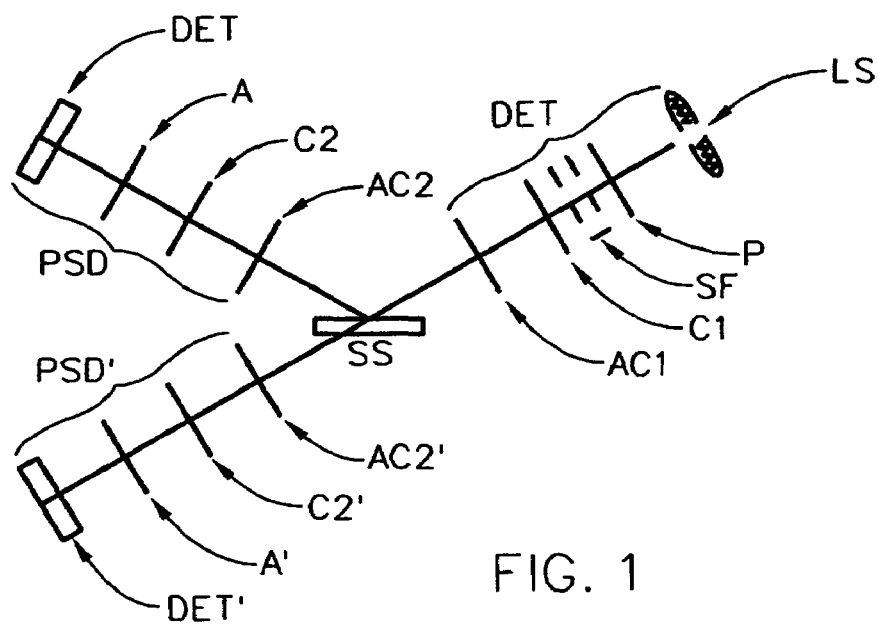
FIG. 1 demonstrates an Ellipsometer System.

To begin, for general insight it should be appreciated that FIG. 1 demonstrates an ellipsometer system which can be applied to investigate a substrate sytsem (SS). Shown for both Reflection and Transmission are, sequentially:

a. a Source of a beam electromagnetic radiation (LS);
b. a Polarizer element (P);
c. optionally a compensator element (C1);
d. (additional element(s)) (AC1);
e. a substrate system (SS);
f. (additional element(s)) (AC2);
g. optionally a compensator element (C2);
h. an Analyzer element (A); and
i. a Detector System (DET).

It is noted that the elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the disclosed invention Disclosure, Substrate Process Chamber Input (WI) and Output (WO) Window means. Note the locations of electromagnetic beams (EMI) and (EMO).

Figure 2A:
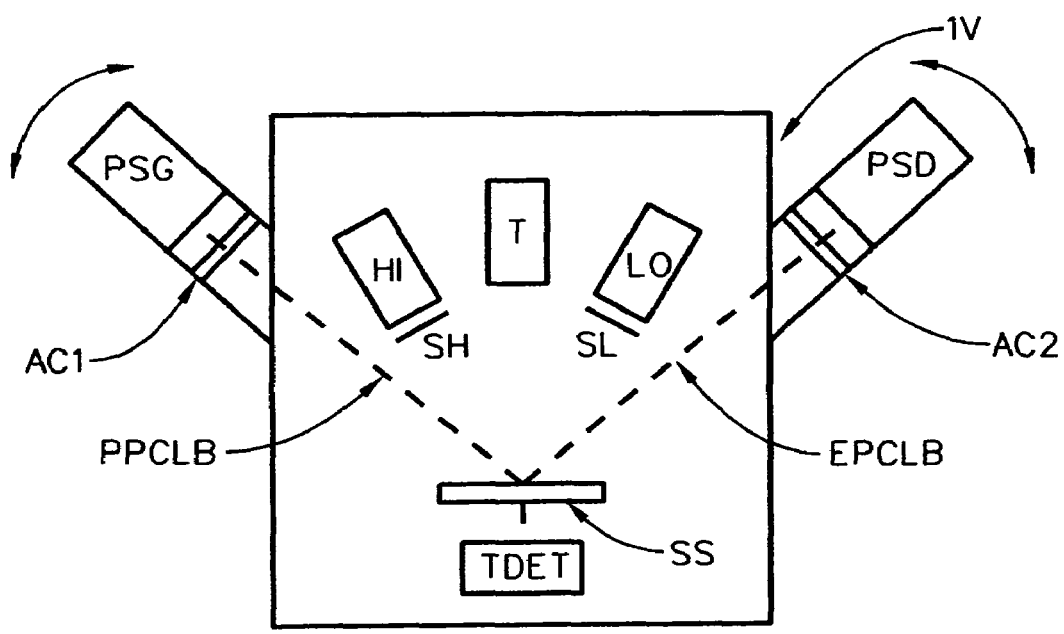
FIG. 2a demonstrates a Substrate Processing Chamber.
Figure 2B:
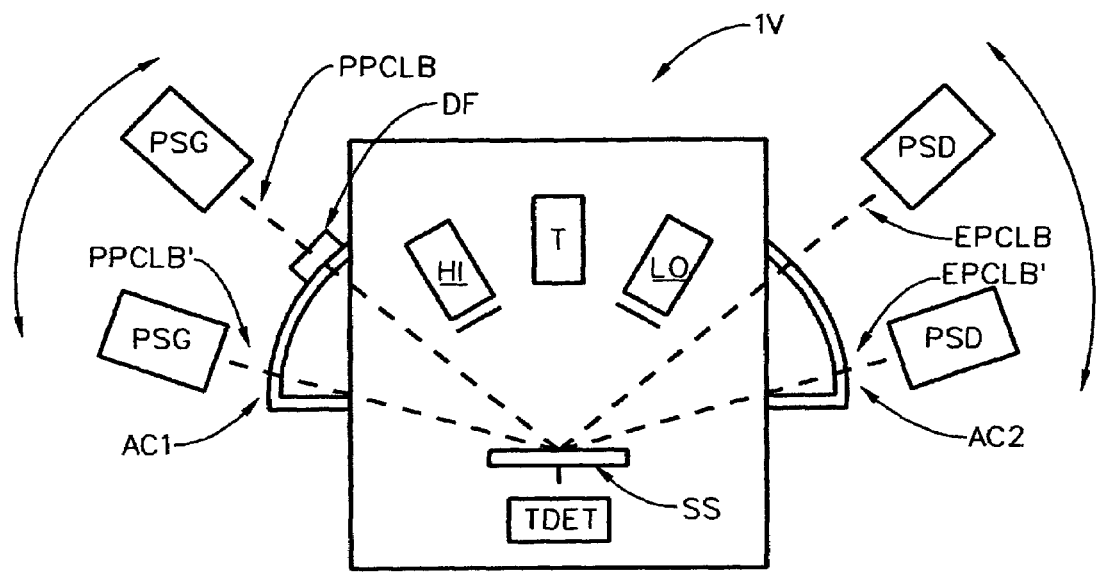
FIG. 2b demonstrates a Substrate Processing Chamber with provision for changing Angle-of-Incidence of a beam.

FIG. 2a shows a Substrate Process Chamber (1V) with a Substrate (SS) present therein, and including means indicated as (HI) and (LO), each with a Shutter (SH) and (SL) associated therewith, for effecting Substrate (SS) processing, such as fabrication of Multi-layer Interference Bandpass and Band-reject Filters by deposition of materials. The Process Chamber could also be applied to etching of material from the surface of substrates. Affixed to the Substrate Process Chamber (1V) is a Reflection Mode Ellipsometer as shown in FIG. 1. Note the positioning of (AC1) and (AC2) in both FIGS. 1 and 2 for coordination, and that an incident beam (PPCLB) approaches Substrate (SS) and a beam (EPCLB) reflected from said Substrate. While not specifically shown, (it is not the purpose of this Disclosure to describe suitable beam entry and exit means which allow change of the angles of incidence and abd reflection), the FIG. 2b is shown as a possible, non-limiting, configuration which allows change in the angles of incident beam (PP-CLB) and reflected beam (EPCLB). Such can be achieved by, for instance, providing the shown curved (AC1) and (AC2) Windows, (or any functional equivalent), at the right and left sides of the Substrate Process Chamber (1V) which allow beam passage at various Angles of Incidence and Reflection (not shown). This is because in practice of the disclosed invention it is important to have the capability of changing said Angles, in order to arrive at the AOI at which the Surface Plasmon Resonance occurs. FIG. 2b also can be taken to show that two Electromagnetic Radiation Source and Polarizer combinations (PSG's) can be applied, one P-Polarized, and the other not P-Polarized. In practice the P-Polarized beam can be set to be incident on a Sample Surface at the SPR Resonance angle, and another Polarized beam, (eg. can be non-P-Polarized), at an angle perhaps closer to the Brewster angle. Said second Polarized beam can actually be P-Polarized if it is not incident on the sample surface at the SPR Resonant Angle. Both SPR and Conventional Ellipsometric analysis can then be conducted with the two Polarized beams being simultaneously, or sequentially applied.

Figure 2C:
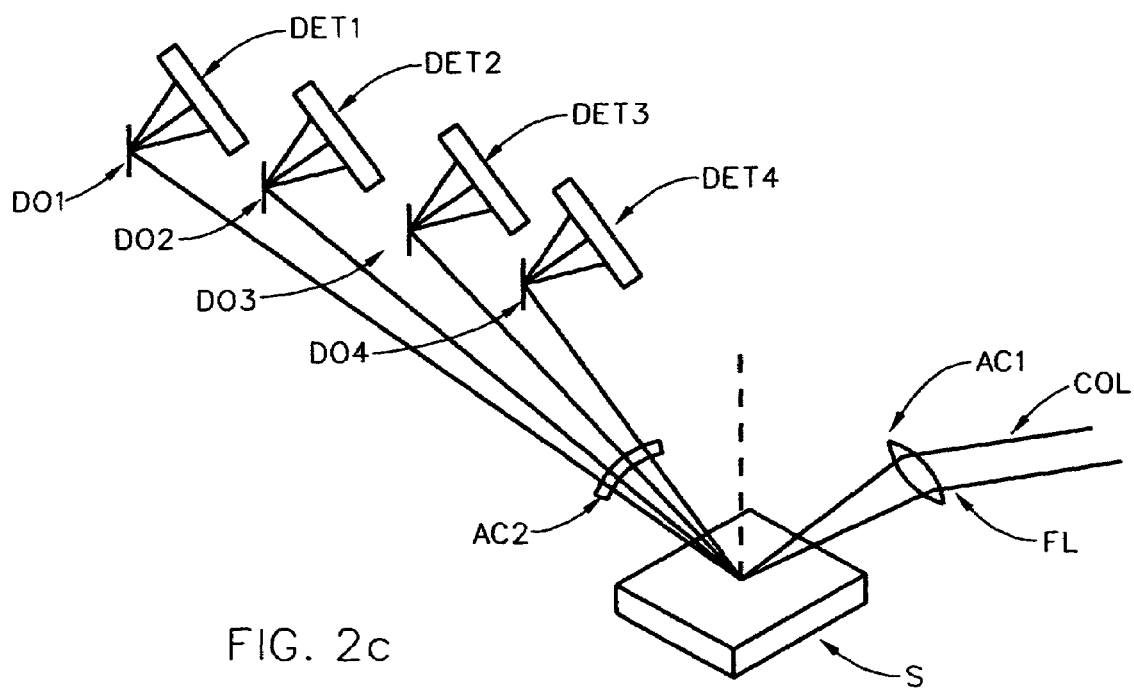
FIG. 2c shows another approach to achieving multiple AOI's which can be applied in a FIG. 2b Substrate Processing Chamber.

FIG. 2c shows another approach to achieving multiple AOI's. A single Colimated (COL) beam can be focused onto a Sample (S), and said input can result in multiple Angles-of-Reflection (AOR's), each of which can be intercepted by different Dispersive Optics, (DO1), (DO2), (DO3), (DO4) and (DO5) and a wavelengths spectrum from each directed into a separate Detectors (DET1), (DET2), (DET3), (DET4) AND (DET5), respectively. Such an arrangement can be applied, via windows, to a Substrate Process Chamber (1V). FIG. 2c also indicates a De-focusing means (DF) can be present to prevent focusing effects of the curved Window (AC1) on a beam of electromagneic radiation passing therethrough.

Figure 2D:
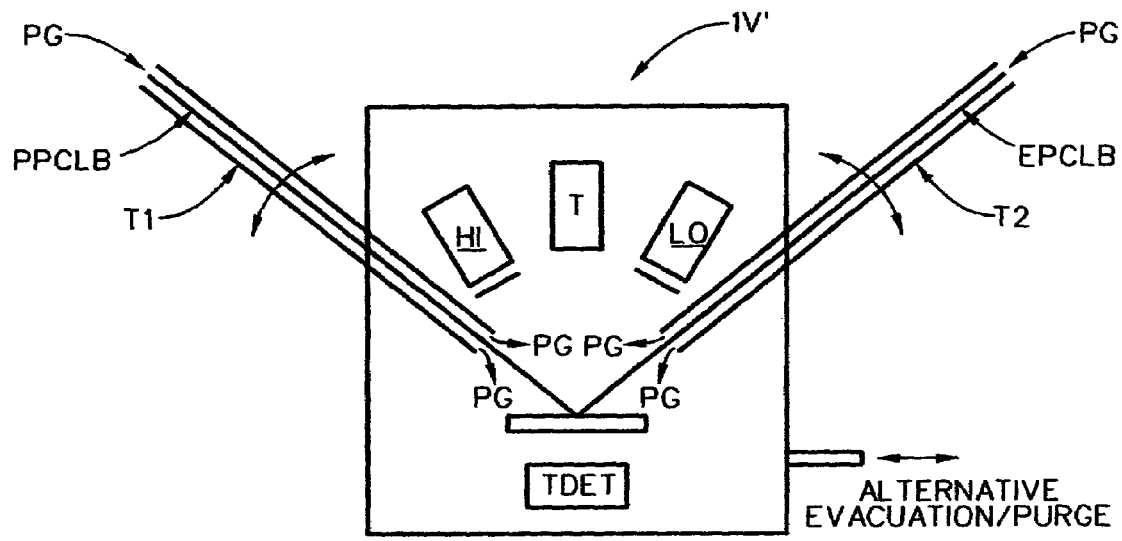
FIG. 2d demonstrates that a purged Substrate Processing Chamber.

FIG. 2d demonstrates that an alternative to providing windows (AC1) (AC2) through which electromagnetic radiation passes, as shown in FIG. 2b and is necessary where the Substrate Process Chamber (1V) is evacuated, is to provide a purged Substrate Process Chamber (1V'). The FIG. 2d embodiment shows Purge Gas (PG) being flowed through Tubes (T1) (T2) through which the incident beam (PPCLB) and reflected beam (EPCLB) electromagnetic beams are passed. The Tubes (T1) and (T2) can be secured to the Purged Substrate Process Chamber (1V') by any means which minimizes escape of the Purging Gas (PG), while allowing change of the AOI and AOR. Use of Purged (1V') rather than evacuated Substrate Process Chamber (1V) can be valuable in, for instance, Chemical Vapor Deposition (CVD) fabrication settings.

The described invention can then be practiced in evacuated or purged Substrate Process Chamber (1V) environments.

Figure 2E:
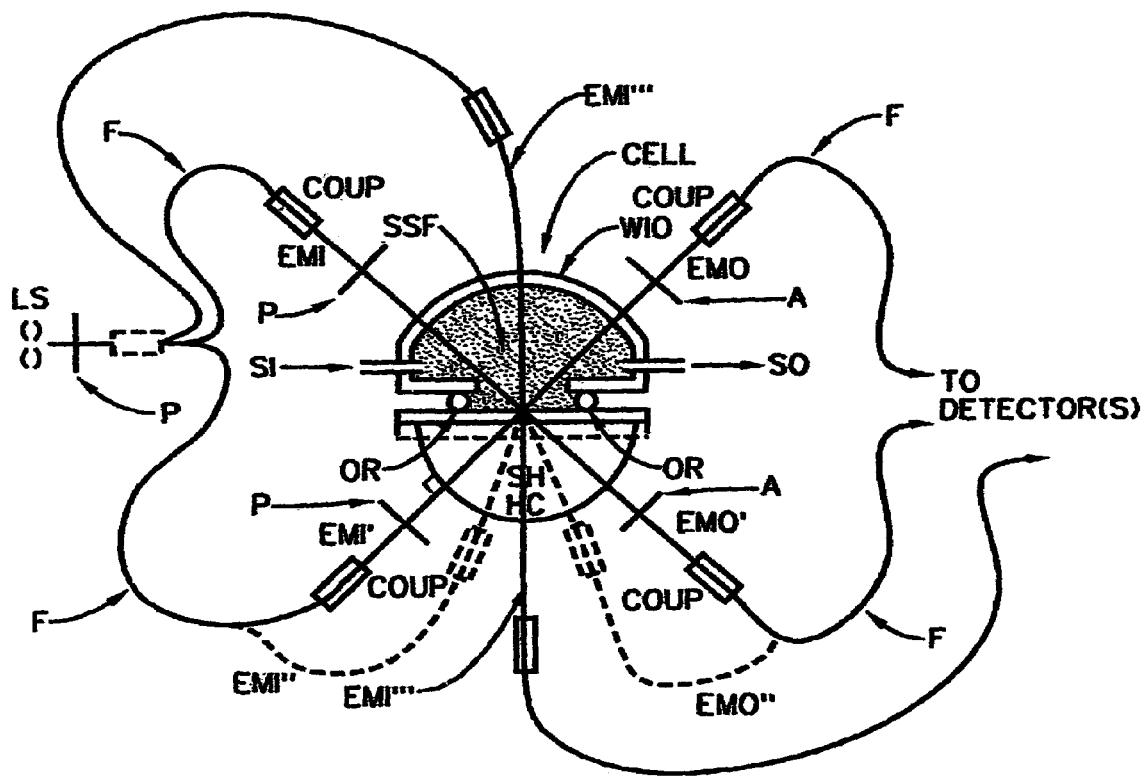
FIG. 2e shows a Cell comprising a surface (SUR) of a sample stage element (STG) which is provided electromagnetic radiation EMI and EMI' from a single source, and further indicates reflected beams EMO and EMO' can be directed to one or more Detector(s).

FIG. 2e shows a (Cell) comprising a surface (SUR) of a sample stage element (STG) which is provided electromagnetic radiation EMI and EMI' or EMI" from a single source via divider means, (or separate sources could be used), and further indicates reflected beams EMO and EMO' are directed to one or more Detector(s). The upper half of said (CELL) is a more conventional system applied in SPR research. It is to be understood that the electromagnetic beams EMI and EMI' can comprise the same or different wavelength content. For instance, the same wavelength content can be present in EMI and EMI" and different angles-of-incidence from above and below utilized, as indicated by EMI and dashed line EMI". Different wavelength content can also be present in EMI and EMI". Where different wavelength content is present, the beams EMI and EMI' can be applied at the same angle-of-incidence, however, in this case the same wavelength content could be present and the purpose behind the configuration being solely to gain data pertaining to top and bottom aspects of a sample atop the surface of the sample stage element (STG). Normal angle of incidence electromagnetic beam EMI''' is indicated as present as well, but no Polarizer or Analyzer is typically present in the EMI''' beam locus. That is EMI''' is a Transmission Intensity beam used to monitor sample absorbance. Note that optical fibers (F) and Couplers (COUP) can be utilized to guide incident and reflected electromagnetic beams. Also note that Analyzer(s) (A), Polarizers (P) and optional Compensator(s) (C1) (C2) along with the Detectors(s) indicated as shown in FIG. 1, are assumed present in FIG. 2e as functionally required. Note, where different wavelengths are to be provided in the multiple electromagnetic beams, utilizing a single source of electromagnetic radiation in combination with Couplers which including functional filtering means, is a possibility. In use fluid containing analyte (SSF) is flowed into (SI) and exits via (SO). Analyte deposits onto the Upper Surface between the "OR" rings and Surface Plasmon Resonance and and Conventional Elipsometry techniques can be applied in analysis as desxcribe above with respect to other systems.

Calculated results are shown in FIGS. 3a, 3b, 4a-4h and 5a and 5b, for Gold deposited onto BK-7 Glass. Said results are exemplary of how ellipsometric PSI and DELTA provide very high sensitivity to surface change at a Surface Plasmon Resonance (SPR) angle-of-incidence.

Figure 3A:
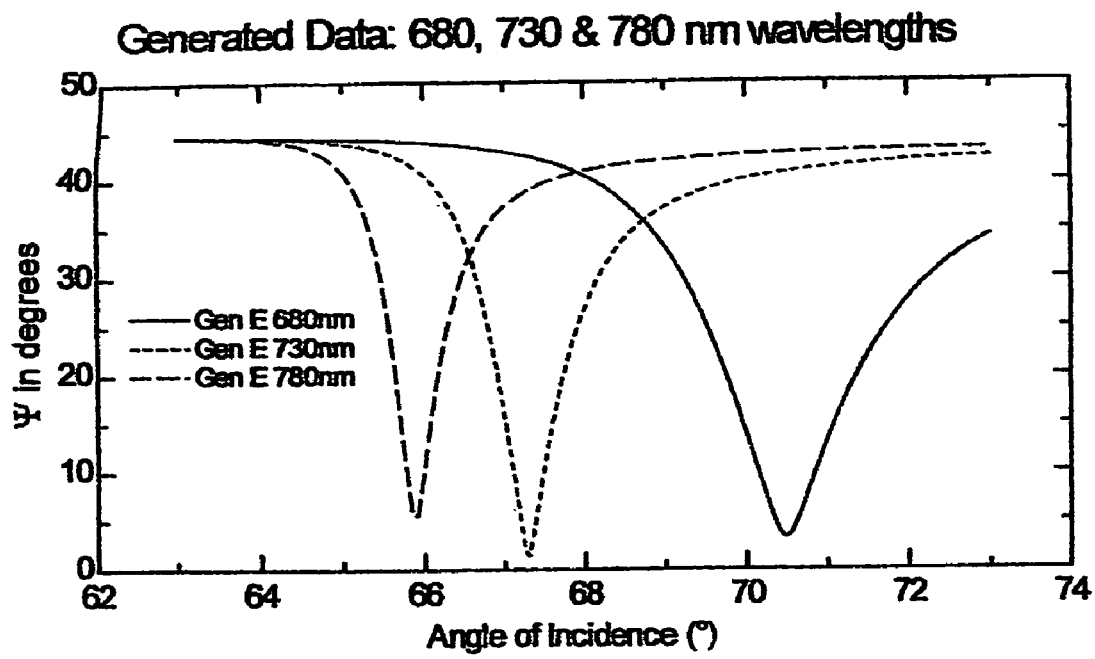
FIGS. 3a and 3b demonstrate ellipsometric PSI and DELTA for BK7 Glass with 50 nm of Gold on its surface, as a function of Angle-of-Incidence, and at 680, 730 and 780 nm.
Figure 3B:
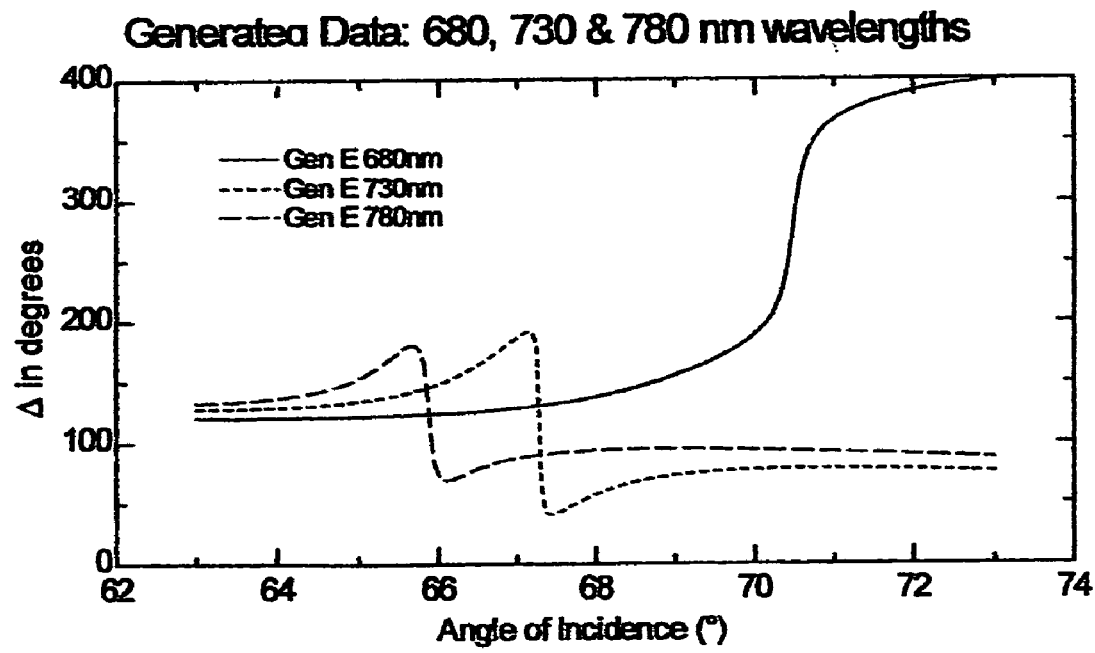

FIGS. 3a and 3b demonstrate ellipsometric PSI and DELTA for BK7 Glass with 50 nm of Gold on its surface, as a function of Angle-of-Incidence, and at 680, 730 and 780 nm. Note in particular the very steep slope of the FIG. 3b DELTA vs. AOI.

Figure 4B:
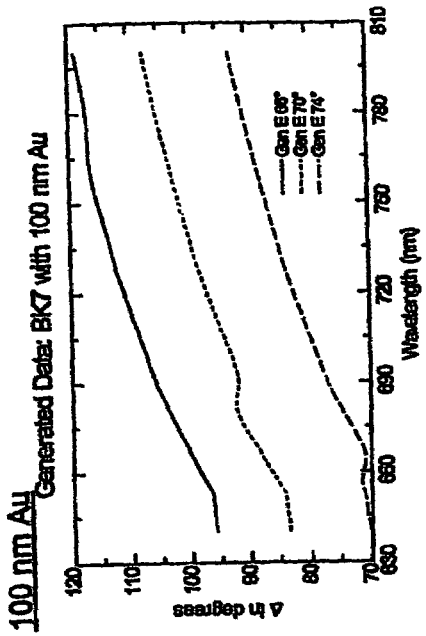
FIGS. 4a-4h demonstrate ellipsometric PSI and DELTA vs. Wavelength, at Angles-of-Incidence of 66, 70 and 74 degrees to a BK-7 Glass Prism upon which is deposited Gold.
Figure 4D:
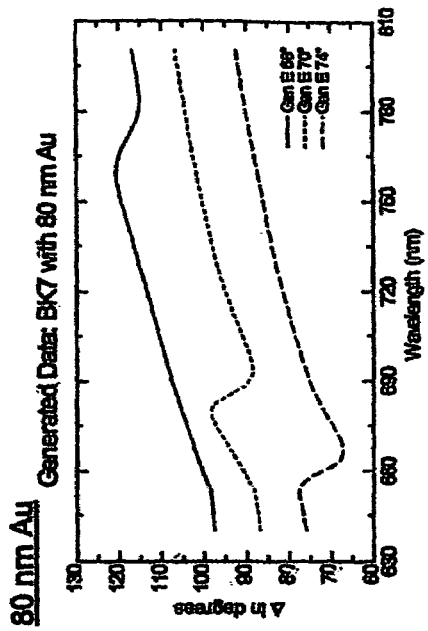
Figure 4A:
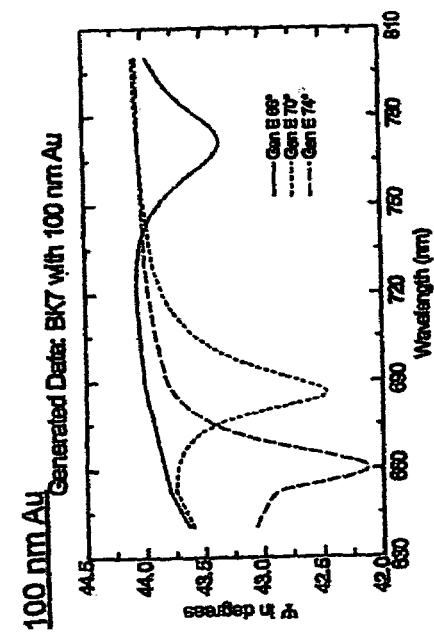
Figure 4C:
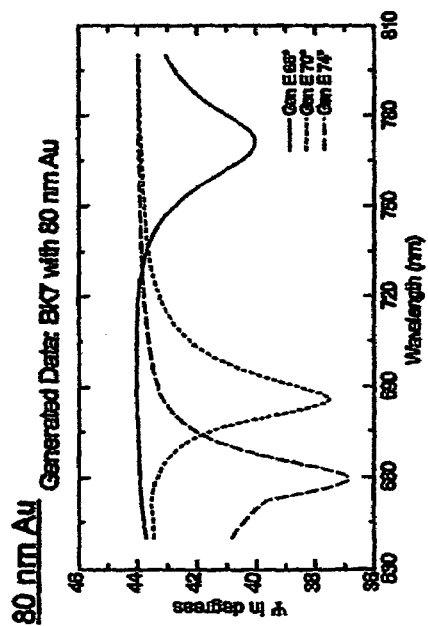
Figure 4F:
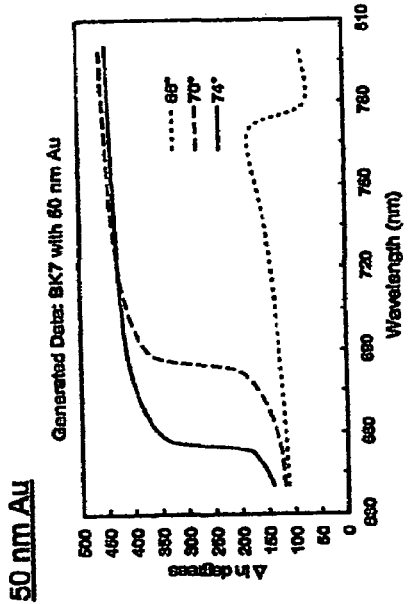
Figure 4E:
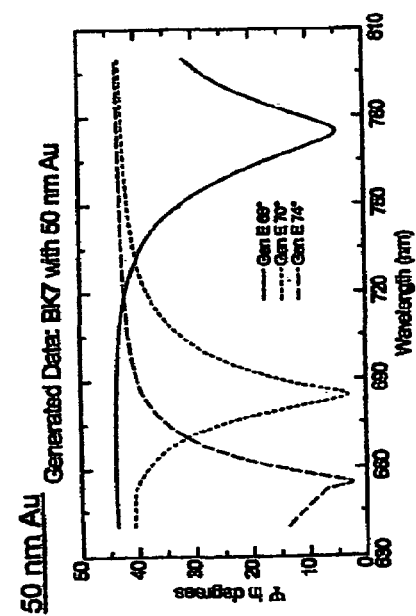
Figure 4H:
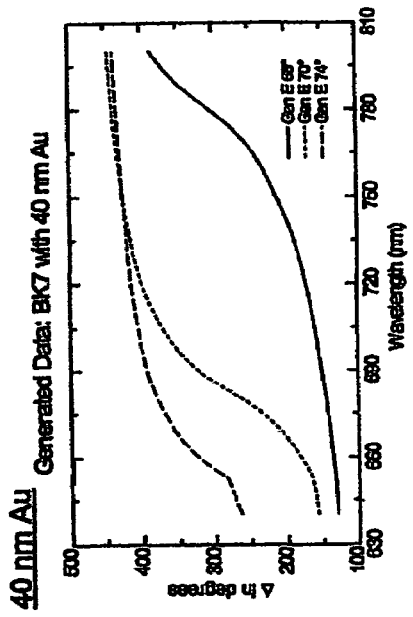
Figure 4G:
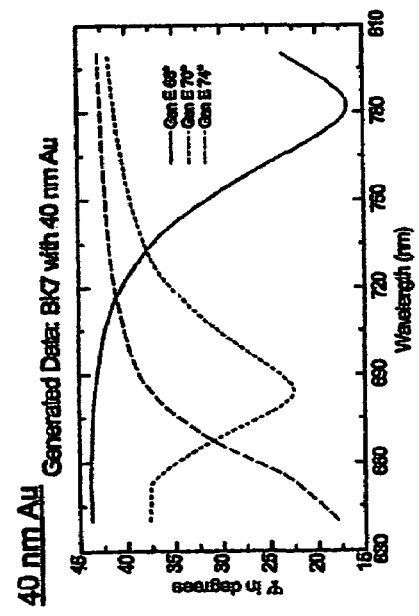
Figure 5A:
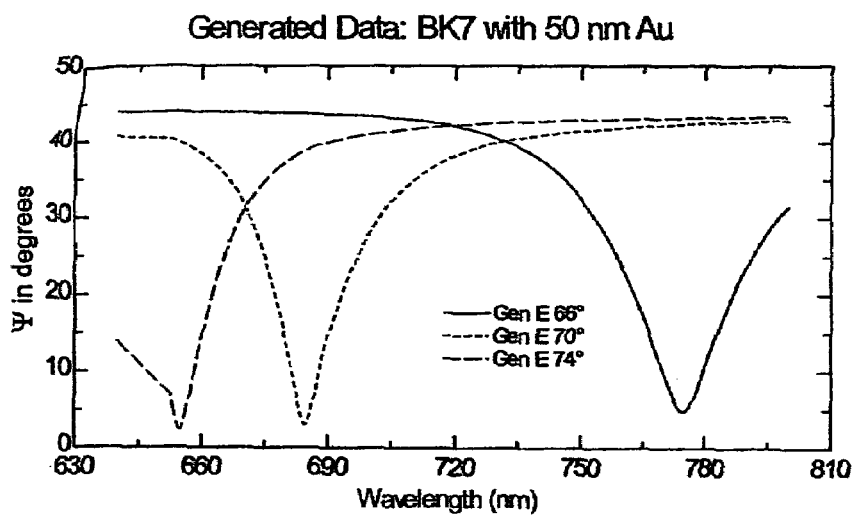
FIGS. 5a and 5b show expanded forms of FIGS. 4a and 4f.
Figure 5B:
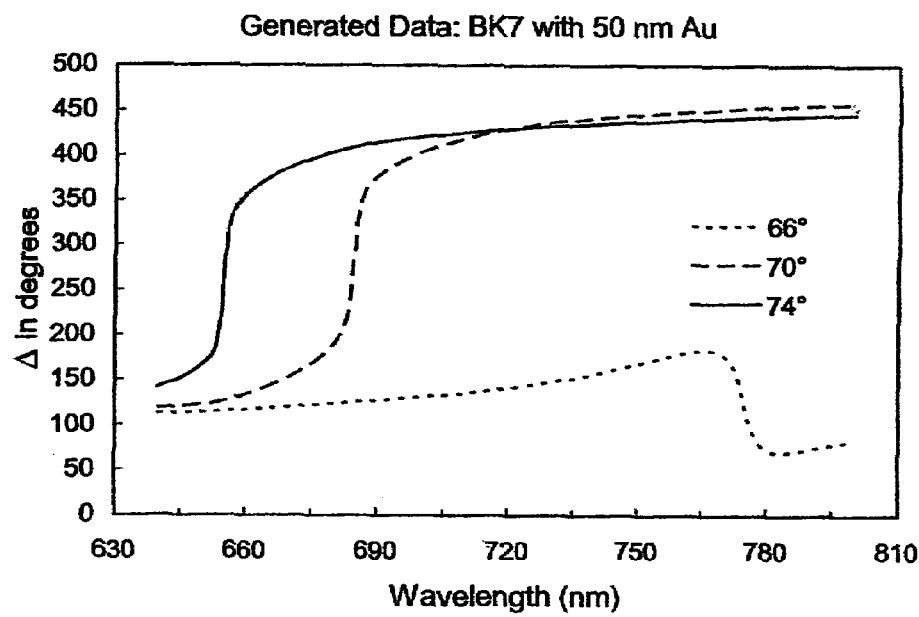

FIGS. 4a-4h demonstrate ellipsometric PSI and DELTA vs. Wavelength, at Angles-of-Incidence of 66, 70 and 74 degrees to a BK-7 Glass Prism upon which is deposited Gold. FIGS. 4a and 4b show ellipsometric PSI and DELTA for the case where 100 nm of Gold is deposited onto the investigated surface, FIGS. 4c and 4d show the results where 80 nm of Gold is deposited, FIGS. 4e and 4f show the case where 50 nm of Gold are present and FIGS. 4g and 4h show the results for the case where 40 nm of Gold is present. Note in FIG. 4f the very steep slope in DELTA for the 66 and 70 Degree AOI's, which is not present in the other, (ie. 4b, 4d and 4h DELTA plots). Where results like shown in FIG. 4f are present the ellipsometric DELTA provides extremely high sensitivity to change in surface properties of a sample. However, FIGS. 4b, 4d and 4h show that the steep slope in ellipsometric DELTA is not always observed. FIGS. 4a, 4c, 4e and 4g show that reasonable sensitivity in ellipsometric PSI is present for all thicknesses of Gold. FIGS. 5a and 5b show expanded forms of FIGS. 4e and 4f.

It should be appreciated that the disclosed invention can be applied to fabrication of thin films via deposition of material onto, or etching material from a substrate, as well as in monitoring analyte material which deposits onto a stage from an analyte containing fluid, (eg. liquid), sample. The very high sensitivity of ellipsometric PSI and/or DELTA at an SPR condition enhances the capability of ellipsometry to detect very thin layers of material deposited onto or removed from a substrate.

It is also disclosed that the described methodology can be applied to samples after they have been fabricated.

The terminology "Plasmon" is to be interpreted sufficiently broadly to include "Polaritons".

It is also conceived that the extra data provided by plasmons or polaritrons could serve to break correlation between thickness and refractive index, which correlation is inherrant in conventional single sample analysis ellipsometry.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of monitoring deposition to, or removal of material from a sample surface, said sample comprising material which demonstrates a negative e1 at some wavelength range, comprising the steps of:
   a) providing an ellipsometer system comprising a source of electromagnetic radiation, a polarizer, a sample supporting stage, an analyzer and a detector and means for changing the angle-of-incidence at which the beam approaches said sample surface;
   b) placing a sample onto said sample supporting stage and by adjusting said polarizer, providing incident P-Polarized electromagnetic radiation to said sample surface, and while monitoring P-Polarized electromagnetic radiation reflected from said sample surface adjusting the angle-of-incidence until, at the wavelength being utilized surface plasmon resonance occurs as evidenced by a large change in intensity or a determined ellipsometric PSI and/or DELTA, thereby indicating that the surface plasmon resonance angle-of-incidence has been identified;
   c) while material deposits onto or is removed from said sample surface, monitoring change in the ellipsometric PSI and/or DELTA which results from the P-Polarized electromagnetic radiation;
   d) said method further comprising providing incident non-P-Polarized electromagnetic radiation at the SPR Resonance angle-of-incidence, or electromagnetic radiation of any polarization other than said SPR resonance angle-of-incidence,
   said electromagnetic radiation being of any wavelength, onto said sample surface such that it reflects into the same, or another detector, and determining a conventional ellipsometric PSI and/or DELTA therefrom; and
   interpreting changes in said ellipsometric PSI's and/or DELTA's to indicate deposition of, or removal of material from said sample surface.

2. A method as in claim 1 in which the P-Polarized and non-P-Polarized electromagnetic radiation are simultaneously applied to said sample surface.

3. A method as in claim 1 in which the P-Polarized and non-P-Polarized electromagnetic radiation are sequentially applied to said sample surface.

4. A method as in claim 1 in which the P-Polarized and non-P-Polarized electromagnetic radiation are incident on said sample surface at the same angle-of-incidence.

5. A method as in claim 1 in which the P-Polarized, and another Polarized electromagnetic radiation are incident on said sample surface at different angles-of-incidence.

6. A method as in claim 1 in which at least one of the P-Polarized and non-P-Polarized beams of electromagnetic radiation comprise infrared wavelengths.

7. A method as in claim 1 in whcih said process and wittness substrates are each independently selected from the group consisting of:
   gold;
   silver;
   iridium;
   silicon;
   gallium arsenide;
   semiconductor with surface insulator layer(s);
   doped semiconductor;
   compensated semiconductor;
   SiC;
   AIN;
   SiO2 (quartz);
   hexagonal BN;
   cubic BN;
   Graphite;
   Heavily doped binary, ternary, and quaternary alloys of compound 3/I semiconductors.

8. A method of monitoring deposition to, or removal of material from a process sample surface comprising the steps of:
   a) providing an ellipsometer system comprising a source of electromagnetic radiation, a polarizer, a sample supporting stage, an analyzer and a detector and means for changing the angle-of-incidence at whcih the beam approaches said sample surface;
   b) placing a process sample and a wittness sample onto said sample supporting stage and by adjusting said polarizer, providing incident P-Polarized electromagnetic radiation to said witness sample surface, and while monitoring P-Polarized electromagnetic radiation reflected from said wittness sample surface adjusting the angle-of-incidence until surface plasmon resonance occures as evidenced by a large change in intensity or a determined ellipsometric PSI and/or DELTA, thereby indicating that the surface plasmon resonance angle-of-incidence has been identified;
   c) while material is caused to deposit onto or is removed from said process sample and wittness surfaces, monitoring change in the ellipsometric PSI and/or DELTA which results from the P-Polarized electromagnetic radiation;
   d) said method further comprising providing incident non-P-Polarized electromagnetic radiation at the SPR Resonance angle-of-incidence, or electromagnetic radiation of any polarization at other than said SPR resonance angle-of-incidence onto said process sample surface such that it reflects into the same, or another detector, and determining conventional ellipsometric PSI and/or DELTA therefrom; and
   interpreting changes in said wittness and process sample ellipsometric PSI's and/or DELTA's to indicate deposition of, or removal of material from said process sample surface.

9. A method as in claim 8 in which the P-Polarized and non-P-Polarized electromagnetic radiation are simultaneously applied to said sample surface.

10. A method as in claim 8 in which the P-Polarized and non-P-Polarized electromagnetic radiation are sequentially applied to said sample surface.

11. A method as in claim 8 in whcih the P-Polarized and non-P-Polarized electromagnetic radiation are incident on said sample surface at the same angle-of-incidence.

12. A method as in claim 8 in which the P-Polarized, and another Polarized electromagnetic radiation are incident on said sample surface at different angles-of-incidence.

13. A method as in claim 8 in which at least one of the P-Polarized and non-P-Polarized beams of electromagnetic radiation comprise infrared wavelengths.

14. A method as in claim 8 in which said process and wittness substrates are each independently selected from the group consisting of:
   gold;
   silver;
   iridium;
   silicon;
   gallium arsenide;
   semiconductor with surface insulator layer(s);
   doped semiconductor;

compensated semiconductor;
SiC;
AlN;
SiO2 (quartz);
hexagonal BN;
cubic BN;
Graphite;
Heavily doped binary, ternary, and quaternary alloys of compound 3/I semiconductors.

15. A method as in claim 1 in which said step of providing an ellipsometer system further comprises providing at least one compensator at a location selected from group consisting of
between said polarizer and sample supporting stage; and
between said sample supporting stage and said analyzer.

16. A method of monitoring the deposition or removal of material from the surface of a substrate comprising the steps of:
  a) while material is being deposited or removed from said substrate surface, by causing electromagnetic radiation to impinge on, interact with and then enter a detector:
    obtaining ellipsometric data using P-Polarized electromagnetic radiation directed to a substrate surface at a Surface Plasmon Resonance Resonance angle-of-incidence to said sample surface, and
    simultaneously or sequentially obtaining conventional ellipsometric data using other than P-Polarized electromagnetic radiation applied at said SPR Resonance angle-of-incidence, or electromagnetic radiation of any Polarization applied at other than said SPR Resonance angle-of-incidence;
  b) analyzing said data to arrive at a thickness for deposited or removed material.

17. A method as in claim 16 which further comprises the step of controlling deposition or removal of material using said ellipsometric data.

18. A method as in claim 16 in which said ellipsometric data obtained using P-Polarized electromagnetic radiation at the SPR resonance angle-of-incidence and data, and said data simultaneously or sequentially obtaining using other than P-Polarized electromagnetic radiation applied at said SPR Resonance angle-of-incidence, or electromagnetic radiation of any Polarization applied at other than said SPR Resonance angle-of-incidence, are analyzed simultaneously.

19. A method of analyzing samples comprising the steps of:
  a) providing a sample upon which a material has been deposited or removed, and by causing electromagnetic radiation to impinge on, interact with and then enter a detector:
    obtaining ellipsometric data using P-Polarized electromagnetic radiation directed to a substrate surface at a Surface Plasmon Resonance Resonance angle-of-incidence to said sample surface, and
    simultaneously or sequentially obtaining conventional ellipsometric data using other than P-Polarized electromagnetic radiation applied at said SPR Resonance angle-of-incidence, or electromagneic radiation of any Polarization applied at other than said SPR Resonance angle-of-incidence;
  b) analyzing said data to arrive at a thickness for deposited or removed material.

* * * * *